United States Patent [19]

McManus et al.

[11] Patent Number: 5,501,080
[45] Date of Patent: Mar. 26, 1996

[54] SELF-CONTAINED CRYOGENIC GAS SAMPLING APPARATUS AND METHOD

[75] Inventors: Gary J. McManus; Billy G. Motes; Susan K. Bird, all of Idaho Falls; Dale K. Kotter, Shelley, all of Id.

[73] Assignee: Lockheed Idaho Technologies Company, Idaho Falls, Id.

[21] Appl. No.: 355,689

[22] Filed: Dec. 14, 1994

[51] Int. Cl.⁶ ........................................ B01D 8/00
[52] U.S. Cl. .................. 62/55.5; 62/235.1; 73/863.11
[58] Field of Search ............................ 62/51.1, 55.5, 62/235.5; 73/863.11

[56] References Cited

U.S. PATENT DOCUMENTS

| | | |
|---|---|---|
| T976,001 | 11/1978 | Schuck . |
| 3,104,542 | 9/1963 | Scoggins . |
| 3,272,258 | 9/1966 | Bourquard ............................. 62/51.1 |
| 3,299,700 | 1/1967 | Stout, Jr. . |
| 3,461,727 | 8/1969 | Everhard et al. . |
| 3,673,871 | 7/1972 | Randle et al. . |
| 3,751,984 | 8/1973 | Rennie . |
| 3,938,391 | 2/1976 | Winkler . |
| 4,008,620 | 2/1977 | Narato et al. . |
| 4,137,773 | 2/1979 | Loncaric . |
| 4,226,115 | 10/1980 | Williams et al. . |
| 4,283,948 | 8/1981 | Longsworth . |
| 4,425,811 | 1/1984 | Chatzipetros et al. . |
| 4,438,653 | 5/1984 | Beentjes . |
| 4,468,973 | 9/1984 | Iannacchione et al. . |
| 4,516,435 | 5/1985 | Outlaw et al. . |
| 4,593,530 | 6/1986 | Longsworth . |
| 4,610,169 | 9/1986 | Clavell, Jr. . |
| 4,756,200 | 7/1988 | Ramser et al. . |
| 4,783,990 | 11/1988 | Eberle et al. . |
| 4,966,016 | 10/1990 | Bartlett . |
| 4,991,449 | 2/1991 | Dieguez . |
| 4,998,433 | 3/1991 | Stumpf et al. . |
| 5,275,007 | 1/1994 | Neeser ..................................... 62/51.1 |
| 5,293,750 | 3/1994 | Tamura et al. ........................... 62/51.1 |

*Primary Examiner*—Ronald C. Capossela
*Attorney, Agent, or Firm*—Spensley Horn Jubas & Lubitz

[57] ABSTRACT

Apparatus for obtaining a whole gas sample, composed of: a sample vessel having an inlet for receiving a gas sample; a controllable valve mounted for controllably opening and closing the inlet; a valve control coupled to the valve for opening and closing the valve at selected times; a portable power source connected for supplying operating power to the valve control; and a cryogenic coolant in thermal communication with the vessel for cooling the interior of the vessel to cryogenic temperatures.

A method of obtaining an air sample using the apparatus described above, by: placing the apparatus at a location at which the sample is to be obtained; operating the valve control to open the valve at a selected time and close the valve at a selected subsequent time; and between the selected times maintaining the vessel at a cryogenic temperature by heat exchange with the coolant.

12 Claims, 2 Drawing Sheets

SELF-CONTAINED CRYOGENIC GAS SAMPLING APPARATUS AND METHOD

ORIGIN OF THE INVENTION

This invention was conceived or first reduced to practice in the course of, or under Contract Number DE-AC07-841D12435 between the Westinghouse Idaho Nuclear Company and the United States Government, represented by the Department of Energy. The United States Government may have rights in this invention.

BACKGROUND OF THE INVENTION

The present invention relates to the taking of gas samples, particularly in hazardous or remote environments.

Air sampling is a practice employed for many purposes, including air quality and plant operation monitoring. If often occurs that an air sample must be taken at a location containing hazardous, toxic and/or volatile, and particularly explosive, components. In addition, it is frequently desired to obtain samples in unpopulated locations where manmade power sources are not available and the sampling equipment must be left unattended.

While a large number of air sampling systems have been proposed and developed, there is presently no system which deals with all of the above-noted conditions in a completely satisfactory manner.

SUMMARY OF THE INVENTION

It is an object of the present invention to provide a sampling apparatus and method which can be used satisfactorily under a wide variety of adverse conditions for sampling air containing any toxic, radioactive, or volatile components.

Another object of the invention is to provide an apparatus and method which can be controlled to take an air sample at a selected time without generating any electrical discharge which could ignite explosive components.

Another object of the invention is to obtain a large volume sample with a small, portable apparatus.

A further object of the invention is to provide a sampling apparatus which can operate unattended in a hazardous or toxic environment, and in particular which can collect an air sample during a time period between preset starting and ending times.

Another object of the invention is to provide a portable, self-contained apparatus which takes possible relatively long sampling times to allow collection of a sufficient volume of a sample.

Another object of the invention is to provide apparatus which can be easily transported manually.

Another object of the invention is to provide apparatus having a self-contained power source, making possible its installation at inaccessible locations.

Still another object of the invention is to provide a sampling apparatus which can collect a large sample quantity by highly compressing the sample gas without altering the composition of the sample, i.e. without preferential condensation of certain gas components or fractionation of the sample.

The above and other objects are achieved, according to the invention, by apparatus for obtaining a whole gas sample, comprising: a sample vessel having an inlet for receiving a gas sample; a controllable valve mounted for controllably opening and closing the inlet; valve control means coupled to the valve for opening and closing the valve at selected times; a portable power source connected for supplying operating power to the valve control means; a cryogenic coolant; and means containing the coolant and placing the coolant in thermal communication with the vessel for cooling the interior of the vessel to cryogenic temperatures, and by a method of obtaining an air sample using the above-described apparatus, which method includes: placing the apparatus at a location at which the sample is to be obtained; operating the valve control means to open the valve at a selected time and close the valve at a selected subsequent time; and between the selected times maintaining the vessel at a cryogenic temperature by heat exchange with the coolant.

Preferred embodiments of the invention have one or more of the following features:

1) A highly compressed gas sample is collected without concentration of condensible gases. This results in an unfractionated whole air sample and allows a large number of gas constituents to be analyzed from a single sample, even when analytes in the sample vary widely in their boiling points.

2) A highly compressed and high volume unfractionated sample is collected without using electromechanical pumps. This greatly reduces hazards of explosions from electrical sparks and improves the reliability of operation.

3) A highly compressed, unfractionated sample is collected without dependency upon line electrical power. This provides a fully portable sampler and permits access to remote sampling locations.

4) The sampling duration of the cryogenic sampler is extended through the user of a dry shipper liquid nitrogen containment vessel.

5) Automated operation of the cryogenic sampler is provided through the use of a programmable valve controller assembly.

6) Long-term, remote operation of the cryogenic sampler is supported through the use of a solar-based power generation system.

DESCRIPTION OF THE PREFERRED EMBODIMENTS

Figure 1:
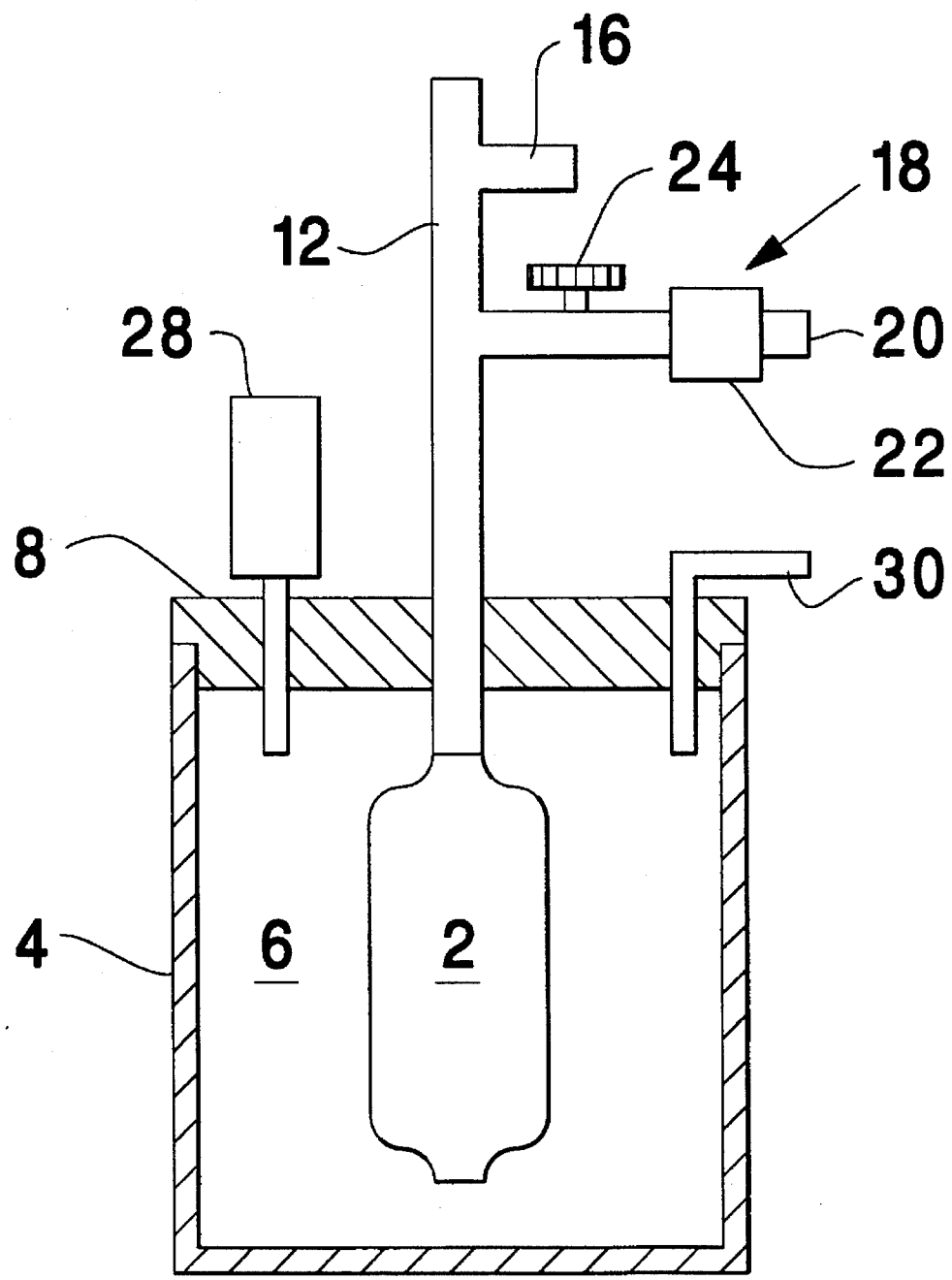
FIG. 1 is an elevational, cross-sectional view illustrating a first embodiment of apparatus according to the invention.

A first embodiment of apparatus, or a sampler, according to the invention, shown in FIG. 1, includes a sample vessel 2 which is installed in a coolant vessel 4 containing a mass of cryogenic coolant 6, such as, for example, liquid nitrogen. Coolant vessel 4 is closed by a lid 8. Sample vessel 2 is suspended from the lower end of a pipe 12 which carries a pressure relief valve 16 and a sample inlet unit 18.

Inlet unit 18 includes an inlet opening 20, an electrically controllable valve 22 and a manual shut-off valve 24.

Pipe 12 provides a flow path between the interior of vessel 2, pressure relief valve 16 and inlet opening 20. The path between inlet opening 20 and the interior of vessel 2 is opened or closed by operation of valve 22.

The apparatus shown in FIG. 1 is completed by a pressure relief valve assembly 28 and a tube 30, both of which are mounted in lid 8 and extend between the interior and the exterior of vessel 4.

The coolant vessel has a pressure relief valve 28 to prevent over pressurization of the $LN_2$ reservoir. Tube 30 provides the capability to connect an external liquid nitrogen line to the coolant vessel for refills, without having to remove the lid 8.

For performing a sampling operation, the interior of vessel 2 would preferably first be evacuated as completely as possible, by any suitable technique, after which valves 22 and 24 would be closed. This evacuation could take place at or above room temperature.

Then, the interior of vessel 4 is filled with cryogenic coolant 6 so that the interior of vessel is brought to a very low temperature.

With the apparatus at a selected sampling location, valve 24 is opened. Then, valve 22 is opened at a first preselected time and is maintained open until a second preselected time, at which time valve 22 closes. During the period when valve 22 is open, atmospheric air will be drawn into vessel 2 as a result of the low pressure existing therein. Since the air entering vessel 2 will be cooled to cryogenic temperature, the pressure in vessel 2 will remain at subatmospheric. The rate of flow of air into vessel 2 may be determined by provision of a flow metering device, such as a rotameter, located within inlet opening 20.

The period of operability of the apparatus will depend on the length of time during which vessel 2 can be maintained at a suitably low temperature, and this will depend in part on the extent to which coolant 6 is insulated from the surrounding environment. In order to increase the time between deployment of the apparatus and completion of a sampling procedure, vessel 4 is preferably constructed to provide a high degree of thermal insulation, without being unacceptably heavy. According to one preferred embodiment of the invention, these goals are achieved by constructing coolant vessel 4 as a dry shipper vessel. One suitable example of such a dry shipper vessel is manufactured by Taylor-Wharton Company and marketed as Part Number CP65.

Pressure relieve valve 16 only opens if too large a sample is collected. The valve control system is user programmable to protect against sampling periods that exceed vessel containment limits.

After the end of the sampling period, valve 22 closes and the sample remains trapped in vessel 2. However, if the apparatus is not recovered for withdrawal of the sample within an appropriate period of time, coolant 6 will have become depleted and the interior of vessel 2 will begin warming, so that some of the sample will escape to the atmosphere via pressure relief valve 16. However, valve 16 can be set to open at a high pressure, so that only a small quantity of sample will tend to be lost.

Figure 2:
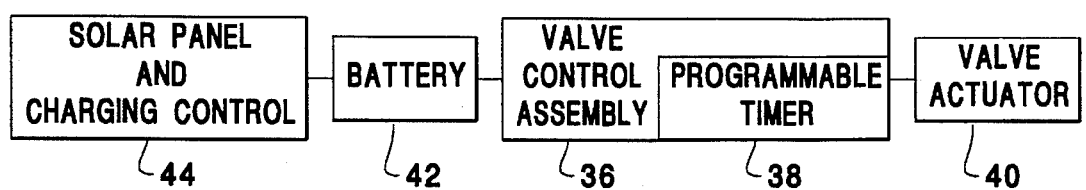
FIG. 2 is a block diagram illustrating the basic components of the electrical system of the apparatus of FIG. 1.
Figure 3:
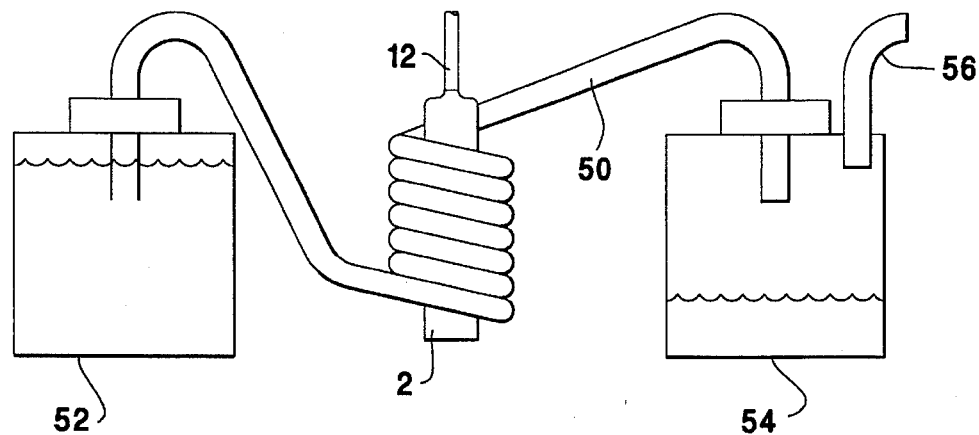
FIG. 3 is an elevational, simplified pictorial view of a second embodiment of apparatus according to the invention.

One embodiment of an electrical system for controlling the operation of the apparatus of FIG. 1 is shown in FIG. 2. This system includes an electrically operated valve control assembly 36 containing a programmable timer 38. Timer 38 is connected to a valve actuator 40 which opens and closes valve 22 of FIG. 1.

Power for operating assembly 36, timer 38 and actuator 40 is supplied by a rechargeable battery 42. According to the present invention, battery 42 is connected, in turn, to a self-contained charging system 44, which preferably includes a solar panel for converting solar radiation into an electric current and a suitable charging control arranged to supply the current generated by the solar panel to battery 42 in a manner to charge battery 42 and maintain battery 42 in its charged state while preventing overcharging of battery 42.

Another embodiment of apparatus according to the invention is illustrated in FIG. 3. In this embodiment, sample vessel 2 is surrounded by a tube 50 which is formed to define a coiled helix surrounding vessel 2 and extending between a cryogenic coolant supply vessel 52 and a cryogenic coolant recovery vessel 54. When vessel 2 is to be cooled, cryogenic coolant may be caused to flow through tube 50 at a controlled rate from vessel 52 to vessel 54. The flow of cryogenic coolant may be controlled to maintain vessel 2 at a fixed temperature, resulting in an approximately constant rate of flow of the air sample into vessel 2. Cryogenic coolant flowing into vessel 54 may be recycled for subsequent sample collection. As cryogenic coolant in vessel 54 evaporates, the coolant in gaseous form can escape via a vent 56.

In a practical embodiment of the apparatus shown in FIG. 3, vessels 2, 52 and 54 could all be housed in a common, insulated container.

In the embodiment shown in FIG. 3, pipe 12 and valves 22 and 24 are identical to those of the embodiment of FIG. 1.

Sampling periods are a direct function of the ability to maintain appropriate levels of liquid nitrogen in the sampler. As the liquid nitrogen depletes, the differential pressure and "pumping effort" decrease. By replacing the liquid nitrogen vessel of FIG. 1 with a confined flow system of FIG. 3, the requirement of refilling the coolant vessel and losing sampling capabilities no longer exists. The use of the confined flow system offers other advantages such as: the flowrate of the air sample remains constant due to the continual flow of liquid nitrogen through the loop surrounding the sample cylinder, whereas with the use of the liquid nitrogen vessel of FIG. 1, the sample flowrate drops as the level of the liquid nitrogen decreases. The confined flow system can be used for sampling in locations where an open container of liquid nitrogen is restricted (such as whole air sampling on board an airplane), and the confined flow system decreases the amount of liquid nitrogen required as the liquid nitrogen is actually being projected from a pressurized vessel through the loop and into another liquid nitrogen vessel and may be recycled again for future sample collection. This would be cost effective particularly for field sampling where multiple samples are required at several locations.

In a preferred practical embodiment of the invention, electric actuator 40 may be constituted by a product manufactured by Whitney, Series 141, and inlet valve 22 may be a two-way ball, one-quarter inch, 6000 psi, also available from Whitney. The valve used in embodiments of the invention should provide bubble-tight, leak free operation at least up to an operating pressure of 5000 psi. Actuator 40 should be installed in a spark-proof housing to permit sampling to be performed in explosive environments.

Also in preferred embodiments of the invention, solar-based charging system 44 can be composed of a Model UPM-880 solar power module marketed by United Solar Systems and the charge controller module can be a Model M-8 marketed by Sun Selector Corp. In general, the solar panel employed should be one which has the ability to generate a sufficient current in deep shadows or under partial foliage cover, which generally requires a parallel solar cell layout with integrated bridging diodes. The panel employed in embodiments of the present invention should be constructed to withstand rugged remote operation.

Preparation of apparatus according to the invention for routine operation requires the generation of reduced pressure within the sample cylinder. The necessary pressure differential is induced, according to ideal gas law principles, by cooling insulated high pressure vessel 2 with liquid nitrogen. The resulting pressure differential produces a pumping effect, which draws the air sample into vessel 2. Unlike conventional freezeout devices, gases with boiling points lower than nitrogen (such as hydrogen and helium) are quantitatively collected because the sampler only permits one-way, bulk non-diffusive flow. Once the sampler is sufficiently filled to the point that low boiling gases might escape, high pressure valve 22 is automatically closed and the insulated high pressure cylinder is allowed to warm to room temperature.

The result is a compressed air vessel 2, pressurized up to 5000 psi, containing more than 100,000 $cm^3$ (STP) of sample in a cylinder no more than 500 $cm^3$ in volume. In addition, the sample is neither depleted in low boiling gases, nor enriched in high boiling point gases such as water, freons, and heavy hydrocarbon vapors. The actual volume of the sample collected is dependent upon the sampling duration and sample flowrate. Samples of accurately known size from a few to nominally 100 liters may be collected, unattended, within 30 minutes up to a period of several hours. The sample containment vessel can then be removed and transported to the laboratory for further analysis.

Hardware for automatic control of the cryogenic sampler includes an electrically actuated inlet valve 22 and valve controller assembly 36. Inlet valve 22 is installed directly on the cryogenic sampier's input line. Assembly 36 is packaged in a separate, portable housing.

Prior to placing the sampler in the field for remote operation, the following preparatory steps must be taken. 1) The sample flowrate is manually set through the adjustment of the rotameter. 2) The assembly 36 is programmed with the day and time (hour/minute) for starting and stopping the sampling process. 3) A cable assembly is installed between the cryogenic sampier's electric valve actuator 40 and the assembly 36 and 4) The cryogenic sampler is provided with a sufficient level of liquid nitrogen in its dry shipper.

The introduction of sample into sample cylinder 2 is initiated when assembly 36 automatically opens sample inlet valve 22. Likewise, when the preprogrammed command is executed, actuator 40 closes inlet valve 22 and terminates the sample process.

Further technical specifications on the operation of the valve controller and electric valve system, include design of remotely controlled inlet valve 22 to meet several critical design specifications, including, pressure ratings to 6000 PSI; corrosive resistant, weather-proof and spark-proof enclosure; ability to operate over extreme temperatures (20° F. to 150° F.); and the use of a blow-out proof stem and ball to ensure safety and reliability.

Electric actuator 40 is selected to provide the capability of operating on low current, 24 Vdc power. To ensure that size restrictions are maintained, a compact permanent magnetic motor with high torque and high efficiency is used. To reduce field maintenance, the gear train of the motor is permanently lubricated and designed for maintenance-free operation. Accurate valve positioning is ensured through the use of a nylon cam and limit switches. The cam is installed on the drive shaft of the motor to determine when a specific position has been reached. The limit switches give exact positioning of the valve and are designed to eliminate the need for manual valve position adjustments. The limit switches also drive additional circuitry to provide electronic feedback of proper valve positioning. An electronic brake is incorporated to stop the motor quickly for precise positioning and to lock the motor to prevent any inadvertent valve stem shift. Other features of the electric actuator include the ability to be installed into a variety of control systems. In a manual mode of operation, a simple switch can control the actuator. In a remote mode of operation, the actuator can be powered directly from assembly 36 or timer 38 without the need for complex interface circuitry.

The dc power source 42 and control logic for operation of the valve may be located in assembly 36. Assembly 36 is packaged in an environmentally sealed and spark-proof cabinet and contains a user programmable timer relay module, a 12/24 vdc battery pack, battery recharge circuitry, a battery status meter, and an operator control/status panel.

The timebase of the programmable timer relay module is based on a quartz crystal with an accuracy of better than ±1 sec/day at 20° C. This timebase or internal digital timer, allows the controller to be easily programmed to cycle valve 22 opened or closed, up to a maximum of eight preset times. The timer circuit interfaces directly to a relay module, which acts as a multiplexer to route the power to the valve actuator. A transfer of the relay contact occurs when the actual time coincides with the programmed time. Once the relay has switched, it will remain in that state until a subsequent programmed command resets it. The timer has a liquid-crystal display which gives the status of the time, day of week, and the position of the relay. In addition, the front panel of the timer/relay module is designed for easy operation with entry buttons for setting days of the week, hours, minutes, clock time, manual switch control, and program entry. In the event the main battery source is lost, all program instructions are retained through a power reserve battery up to a period of 250 hours. Because the relay module switches an inductive load (dc motor), spike suppression devices are installed in-line to protect the timer/relay and to provide immunity to electrical noise.

The housing of assembly 36 has a control panel designed for user friendly operation. A valve status indicator provides verification that the valve is operating properly. Separate status lights show when the valve is closed, opened, or in motion; i.e., motor running.

Assembly 36 contains the dc power source for the cryogenic sampler. Two lead-acid gel cell batteries, each rated at 12 Vdc, 8 amp/hr, are mounted within assembly 36 housing. A power distribution bus provides 12 Vdc for timer/relay operation and 24 Vdc for operation of valve actuator 40. A battery status indicator is also built into assembly 36 control panel. This provides feedback on the storage capacity of the battery and indicates whether recharging is required. Battery charging switching circuitry is designed to provide two methods for charging the batteries. First, an ac charging circuit can be activated if an ac power source is available. Second, appropriate connectors and cables are supplied for connecting and activating charging system 44. Battery capacity has been selected to provide up to five days of field operation without the need for recharging.

For long term remote operation of the cryogenic sampler, it is necessary to have the capability for on-site recharging of the batteries. To provide the capability of recharging batteries without the use of line power or bulky fuelpowered generators, a solar-based charging system 44 was designed. Although the system was developed using commercial components, they were integrated for optimum, efficiency and adapted to a remote, sampler application. The system is made up of a portable solar panel, a charge controller module, a transient voltage suppressor, interconnection cables, and a valve control assembly interface.

Conventional solar panels are normally manufactured with the array of solar cells connected in series. In contrast, the panel used in the implementation of the solar battery charger was designed with integrated bridging diodes, which connect the cells in parallel. This results in a unit which continues to charge the batteries even in deep shadows or partial foliage cover.

The solar panel is constructed to withstand rugged remote operation. The cell assembly is laminated in a weather resistant composite. Tefzel (TM) (by DuPont) serves as the durable front covering. This results in a very rugged solar panel. It is rated to withstand hail impacts of greater than 50 mph. The light weight construction, with aluminum frame mounting, provides a transportable package for remote site setup.

The solar panel's output voltage is regulated and connected to the batteries with a charge controller module. The charge controller uses state-of-the-art, vendor proprietary circuitry that prevents night time reverse discharge of the batteries without using low-efficiency blocking diodes. The controller module also prevents the batteries from being damaged from overcharging. In addition, it extends the life of the batteries by using a trickle charge technique. This results in a high efficiency solar power system.

Appropriate connectors/interfaces and cables are designed for connecting the solar panel, the charge controller module, and the assembly 36.

The cryogenic sampler has the capability to operate from various selectable power sources, including ac power, stand-alone battery, and solar assisted battery.

The sampler uses passive cryogenic techniques to create a pressure differential; therefore it is not dependent upon electromechanical pumping systems. The elimination of pumps greatly reduces the potential for arcs and explosions. Although portable dc power is used for automatic sampling control, the power supply is fabricated into a stand-alone, environmentally sealed, spark-proof housing. The motorized valve mechanism 22, 40 is also enclosed in a sealed housing assembly. The overall relative cost for spark proofing the sampler is greatly reduced by avoiding electrical pumping and through the use of low-level dc voltages.

The sampler is fabricated with corrosive resistant, stainless steel material. The passive and simple design results in a very rugged system.

Previous portable sampling techniques, such as mechanical pump sampling and evacuated cylinder sampling, result in the collection of a relatively low pressure and volume of sample. With the use of mechanical pumps, unreasonably large compressors would be required to increase sample volume. Likewise, evacuated cylinders can only sample quantities equal to their original volume.

The passive cryogenic sampler, however, has been designed to have two hundred times the sample capacity of an equivalent evacuated cylinder. A typical 500 cm$^3$ sampler can collect up to 100,000 cm$^3$ (STP) of air. This is made possible through the use of a cryogenically created pressure differential, which reacts according to the ideal gas law and allows non-diffusive flow into the sample vessel. The resulting increase in sample capacities is crucial when one needs to separate and purify trace constituents (such as krypton, xenon, methane) before the analyte can be measured.

High volume air samples, when compressed into a small portable sampler vessel, can result in pressures approaching 5000 psi. The sampler has been designed with components rated for 5000 psi or greater. As a safety precaution, the maximum pressure within the sampler is limited to 4800 psig by adjustment of a variable set-point sample cylinder pressure relief valve 16. In the event of opening of the pressure relief valve, only a small amount of sample is lost, as the valve is designed to vent pressures greater than its set point and then automatically reseat.

The sampler according to the invention can be designed to be compact and light weight (less than 20 kg). The sampler can easily be fitted into a backpack for transport into remote terrain that is inaccessible to motorized vehicles. The support battery housing and valve control assembly can also be packaged into a small suitcase unit for easy transportability.

Sampling periods are a direct function of the ability to maintain appropriate levels of liquid nitrogen in the sampler. As the liquid nitrogen depletes, the differential pressure and "pumping effect" decrease. In a remote sampling application, it is therefore critical to optimize the storage life of the liquid nitrogen.

To extend the storage life of the liquid nitrogen, a special dry shipper vessel 4 is used. The sample cylinder is suspended into the dry shipper vessel. Vessel 4 contains both absorbent material for long term retention of liquid nitrogen and an additional reservoir where liquid nitrogen can be filled and placed in direct contact with the sample cylinder. When vessel 2 is fully inserted into the dry shipper vessel, it acts as a seal to prevent leakage and excessive thermal loss.

The use of the dry shipper configuration has the potential to greatly extend the sampling period. In addition, it maintains a long term thermal baseline. Even when the reservoir is fully depleted, the absorbent material continues to maintain marginal cooling and a reduced, yet ongoing, sample flow. As additional liquid nitrogen is placed into vessel 4, the sampler quickly reaches optimum operation because of the reduced temperature gradient that must be overcome.

In summary, the use of a dry shipper vessel provides the capability for long-term, reduced flow rate sampling and/or maintains the sampler in a long term (>48 hours) standby mode. This greatly reduces the amount of liquid nitrogen that must be handled during field operation and provides true portability.

The sampler is designed to use cryogenics to generate an overall vessel pressure differential, which in turn draws in the whole air sample. This differs from conventional cryogenic samplers which freeze out the sample and collect only condensible gases. With the sampler according to the invention, whole air samples are collected independent of their boiling points. This preserved composition permits many laboratory analyses to be performed on widely different analytes, using only a single sample.

The sampler does not rely upon sophisticated sensor technology. The sampler exploits the fundamental properties of fluids rather than complex electromechanical technology. This approach leaves expensive instruments in the laboratory and delivers a preserved sample from the field back to the lab for standardized analyses. This low cost, light weight sampler is ideal for taking many whole air samples at remote locations with minimal logistical support.

Remote, unattended operation of the cryogenic sampler is dependent upon two main factors, namely: 1) improved technology for long-term liquid nitrogen cooling of the sample vessel. This technology has been developed and is described above; and 2) capability to automatically and remotely open and close inlet valve 22 in order to start and terminate the sample process. Operation of the sampler is not dependent upon ac line power.

The capability for automatic valve operation is implemented through the use of a dc powered, electric valve actuator 40 and programmable controller module 36. The electric actuator can be mated to a ¼ inch high-pressure ball valve. The valve/actuator assembly is then installed on the sampler's inlet line. A custom assembly 36 was designed to provide the intelligence for the remote switching of the inlet valve and to provide overall control of the sampler's operation. This was done without the requirement for ac power and bulky support equipment.

For long term (>5 days), remote operation of the cryogenic sampler, it is necessary to have the capability for on-site recharging of the batteries. A solar-based generator system was designed to provide this capability. The solar system uses an advanced photovoltaic power module, with an output of 1.4 amps at 15.6 volts. The output voltage is regulated and applied to the batteries with a charge controller module. The controller module prevents the batteries from being damaged from overcharging. In addition, it extends the life of the batteries by using a trickle charge technique.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in Ell respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for obtaining a whole gas sample, comprising:
   a sample vessel having an inlet for receiving a gas sample;
   a controllable valve mounted in said inlet for controllably opening and closing said inlet;
   valve control means coupled to said valve for opening and closing said valve at selected times;
   a portable power source connected to said valve control means for supplying operating power to said valve control means;
   a cryogenic coolant; and
   means containing said coolant and placing said coolant in thermal communication with said vessel for cooling the interior of said vessel to cryogenic temperatures.

2. Apparatus as defined in claim 1 wherein said portable power source is a rechargeable battery.

3. Apparatus as defined in claim 2 further comprising means including a solar cell disposed for converting solar radiation into electricity and connected for recharging said battery.

4. Apparatus as defined in claim 1 wherein said means containing said coolant include a second vessel in which said sample vessel is installed.

5. Apparatus as defined in claim 4 wherein said second vessel is a dry shipper vessel.

6. Apparatus as defined in claim 1 wherein said coolant is liquid nitrogen.

7. Apparatus as defined in claim 1 wherein the gas sample is an environmental air sample.

8. Apparatus as defined in claim 1 wherein said means containing said coolant maintain a constant quantity of coolant in thermal communication with said sample vessel.

9. Apparatus as defined in claim 8 wherein said means containing said coolant comprise a coolant supply container and a coolant flow tube extending around said sample vessel and connected to said coolant supply container for maintaining a flow of coolant from said supply container and around said sample vessel.

10. Apparatus as defined in claim 9 wherein said tube has the form of a multi-turn coil surrounding said sample vessel.

11. A method of obtaining an air sample using the apparatus defined in claim 1 comprising:
    placing the apparatus at a location at which the sample is to be obtained;
    operating said valve control means to open said valve at a selected time and close said valve at a selected subsequent time; and
    between the selected times maintaining said vessel at a cryogenic temperature by heat exchange with said coolant.

12. Apparatus for obtaining a whole gas sample, comprising:
    a sample vessel having an inlet for receiving a gas sample;
    a controllable valve mounted in said inlet for controllably opening and closing said inlet;
    valve control means coupled to said valve for opening and closing said valve at selected times;
    a portable power source connected to said valve control means for supplying operating power to said valve control means;
    a cryogenic coolant; and
    means containing said coolant and placing said coolant in thermal communication with said vessel for cooling the interior of said vessel to cryogenic temperatures, wherein said sample vessel is removable from said means containing said coolant.

* * * * *